(12) United States Patent
Narisawa

(10) Patent No.: US 6,306,390 B1
(45) Date of Patent: Oct. 23, 2001

(54) ROOT ENDOPHYTE HAVING SOIL DISEASE INHIBITORY ACTIVITY, PROCESS FOR PREPARING SAID ROOT ENDOPHYTE, AND METHOD FOR INHIBITING SOIL DISEASE

(75) Inventor: Kazuhiko Narisawa, Ibaraki (JP)

(73) Assignee: Ibaraki Prefecture, Ibaraki (JP)

( * ) Notice: Subject to any disclaimer, the term of this patent is extended or adjusted under 35 U.S.C. 154(b) by 0 days.

(21) Appl. No.: 09/194,289

(22) PCT Filed: Mar. 23, 1998

(86) PCT No.: PCT/JP98/01247

§ 371 Date: Apr. 12, 1999

§ 102(e) Date: Apr. 12, 1999

(87) PCT Pub. No.: WO98/42823

PCT Pub. Date: Oct. 1, 1998

(30) Foreign Application Priority Data

Mar. 24, 1997 (JP) .................................................... 9-088746

(51) Int. Cl.[7] .................................................... C12N 1/14
(52) U.S. Cl. .......................................... 424/93.4; 424/93.1
(58) Field of Search .................................. 424/93.1, 93.4

(56) References Cited

FOREIGN PATENT DOCUMENTS

| 1-502475 | 8/1989 | (JP) . |
| 8703303 | * 6/1987 | (WO) . |
| 9416076 | * 7/1994 | (WO) . |

OTHER PUBLICATIONS

Hinton et al., Mycopathologia 129(2): 117–125 (1995). (Abstract).*
Zachariah et al., Acta Bot Indica 9(2): 323–324 (1981).*
Pleban et al., European Journal of Plant Pathology 101(6): 665–672 (1995).*
Pleban et al., "Chitinolytic Activity of an Endophytic Strain of Bacillus Cereus", Letter in Applied Microbiology 25:284–288, 1997.
Al–Rawahi et al., "Rhizosphere Competence of *Pythium oligandrum*", Phytopathology, 87(9):951–959, 1997.
Cardoso et al., "Biological Control of Rhizoctonia root Rot of Snap Bean with Binucleate Rhizoctonia–like Fungi", Plant Disease, 71(2):167–170, 1987.
Hoffland et al., "Comparison of Systemic Resistance Induced by Avirulent and Nonpathogenic Pseudomonas Species", Phytopathology, 86(7):757–762, 1996.
Larkin et al., "Supression of Fusarium Wilt of Watermelon by Nonpathogenic *Fusarium oxysporum* and other Micororganisms Recovered from a Disease–Suppressive Soil", Phytopathology, 86(8):812–819, 1996.
Liu et al., "Induction of systemic Resistance in Cucumber by Plant Growth–Promoting Rhizobacteria: Duration of . . . ", Phytopathology, 85(10):1064–1068, 1995.
Mazzola et al., "Effects of Fungal Root Pathogens on the Population Dynamics of Biocontrol Strains of Fluorescent Pseudomonads in the Wheat Rhizosphere", Applied & Environ. Microbio., 57(8):2171–2178, 1991.
Wei et al., "Induced Systemic Rsistance to Cucumber Diseases and Increased Plant Growth by Plant Growth–Promoting Rhizobacteria Under Field Conditions", Phytopathology, 86(2):221–224, 1996.

* cited by examiner

*Primary Examiner*—Jean C. Witz
(74) *Attorney, Agent, or Firm*—Fish & Richardson P.C.

(57) ABSTRACT

Root endophyte which live symbiotically within a root of crops were separated and classified. A medium which cultured the strains were inoculated with a seed of a crop. The seed was allowed to sprout to inoculate the root of the crop with root endophytes. While growing the crop, the soil for growth was inoculated with soil pathogenic bacteria, and the crop was grown for a period necessary for the occurrence of a soil disease. The crop was inspected for pathopoiesis, and root endophytes, which had been inoculated into the root of crop having low severity, were specified and selected. As a result, it was found that some root endophytes can significantly inhibit soil diseases. Among root endophytes, *Heteroconium chaetospira* was found to be particularly effective in inhibiting soil diseases.

3 Claims, 3 Drawing Sheets

ROOT ENDOPHYTE HAVING SOIL DISEASE INHIBITORY ACTIVITY, PROCESS FOR PREPARING SAID ROOT ENDOPHYTE, AND METHOD FOR INHIBITING SOIL DISEASE

TECHNICAL FIELD

The present invention relates to a root endophyte capable of preventing soil-borne diseases, a process for producing said root endophyte, and a method for preventing soil-borne diseases of crops using said root endophyte.

BACKGROUND ART

Continuous cropping causes impairments such as poor growth, reduction of the yield, and deterioration of quality in many crops. Severe impairments sometimes result in death of plants. These impairments resulting from continuous cropping are attributed mainly to soil-borne diseases.

For example, club roots and the yellows of Chinese cabbages are representatives of the soil-borne diseases of Chinese cabbages. The club roots of Chinese cabbages are caused by *Plasmodiophora brassicae*. The fungal spores invade into the roots of Chinese cabbages cultivated on the soil, proliferate there, thereby causing the club root disease. As the name of the disease indicates, clubs are formed in the roots of Chinese cabbages suffering from the disease and the clubs inhibit uptake of water and nutrients by the plants from the soil. Eventually, the growth of Chinese cabbages becomes poor, which leads to reduction of their yield and quality. The yellows of Chinese cabbages is caused by *Verticillium dahliae*, which is a terrestrial fungus. Its spores invade into the roots of Chinese cabbages cultivated on the soil, proliferate there, and cause the yellows. In this disease, *Verticillium dahliae* inhibits formation of chloroplasts in the crop, generation of carotenoid alone progresses, then the plants yellow. As a result, the growth of Chinese cabbages becomes poor, resulting in reduction of their yield and quality. Moreover, *Verticillium dahliae* infects flowers and vegetables other than Chinese cabbages. For example, it causes Verticillium wilt in eggplants and tomatoes.

Conventionally, soil has been disinfected generally using chemicals such as PCNB to prevent soil-borne diseases. However, continuous use of soil fumigants subsequent to continuous cropping has facilitated advent of novel pathogens in the soil, which are highly resistant to soil fumigants. Thus, the efficacy of soil fumigants for the pathogen control is reduced. In addition, chemically synthesized soil fumigants may possibly give harmful influences on the environment encompassing consumers, producers, and ecosystem. Under these circumstances, the use of fumigants tends to decrease.

Recently, attempts have been made to apply biological control, which is regarded as a safe method to prevent soil-borne diseases. The biological control has been performed using fungi such as Trichoderma, Fusarium, bacteria such as Pseudomonas and Bacillus, and actinomycetes such as Streptmyces. These microorganisms are formulated into agents and put into practice mainly in United States. Prevention of various soil-borne diseases by utilizing these microorganisms has been studied, but practically usable effect has not been obtained yet.

These microorganisms generally grow and inhabit in the rhizosphere (many microorganisms live within the soil of a few millimeter thick surrounding the surface of roots of plants), and they prevent soil-borne diseases. Since rhizosphere, which is an interface between roots of plants and soil, is a complex and unstable environment, the stable preventive effect is hardly obtained in many cases. It is difficult to constantly obtain a sufficient preventive effect, particularly, in Japan, where a wide variety of microorganisms live in the soil. Prevention of soil-borne diseases targeting rhizosphere has not been widely spread among farmers.

DISCLOSURE OF THE INVENTION

As described above, soil disinfection using agricultural chemicals such as PCNB is not able to completely prevent soil-borne diseases of crops. Furthermore, such soil disinfection gives an undesirable influence on the environment encompassing humans and the ecosystem. Even the conventional biological control has a problem that the preventive effect cannot be constantly obtained when rhizosphere is targeted as an action site for pathogens. An objective of the present invention is to provide techniques for preventing soil-borne diseases with a constant effect and without harmful influences on humans and environment.

There exist a variety of microorganisms in the soil and plants, and they live with interacting with each other. Most of these microorganisms are non-pathogenic and are not infectious to host plants. Particularly, symbiotical root endophytes (symbiotes) are known to live in the root of plants without causing diseases. Focusing on the characteristics of the root endophytes, the present inventors thought that a novel technique for biological control can be established by changing an action site (battlefield) between pathogenic microorganisms causing soil-borne diseases and endophytes from rizhosphere, which is largely affected by environment, to the inside of roots, which is less affected by environment.

Based on this concept, the present inventors first isolated root endophytes from roots of Chinese cabbages, and investigated a preventive effect on the yellows of Chinese cabbages. Specifically, the inventors isolated symbiotic root endophytes from the root of Chinese cabbages cultivated in the soil free from agricultural chemicals, and cultured them. The root endophytes were identified based on the morphology of their spores, and the microorganisms that could not be identified were classified based on colony types. The culture media of these microorganisms were inoculated with seeds of the Chinese cabbages to allow the seeds to germinate. The root endophytes capable of preventing soil-borne diseases of Chinese cabbages were then inoculated into the roots of the Chinese cabbages. *Verticillium dahliae* was then inoculated into the soil where the Chinese cabbages were grown and the Chinese cabbages were continuously cultivated for a period required for the onset of the yellows. Whether the yellows developed in the Chinese cabbages was examined and the root endophytes that were inoculated into the roots showing a low incidence rate of the yellows were identified and selected. As a result, the inventors found that some of the root endophytes inoculated into the roots of the Chinese cabbages remarkably prevented the yellows. In other words, the yellows never developed or the incidence rate of the yellows was remarkably low. Among the root endophytes having the ability to prevent yellows of Chinese cabbages, *Heteroconium chaetospira* was found to be particularly effective to prevent the yellows of Chinese cabbages.

The inventors also examined whether *Heteroconium chaetospira* prevents not only the yellows but also club root diseases of Chinese cabbages, cabbages, and 'chingensai'. Specifically, the culture medium of *Heteroconium chaetospira* was inoculated with seeds of these plants to germinate the seeds. The roots of the plants were then allowed to be inoculated with the fungus. Pathogenic fungus of the club root disease were inoculated into the soil on which the plants were grown and the plants were subsequently allowed to grow for the period required for onset of the club root disease. The development of the disease was then examined. As a result, the inventors found that *Heteroconium chaetospira* notably prevented the club root disease as well as the yellows in Chinese cabbages, cabbages, and 'chingensai'.

Furthermore, the inventors found that, when *Heteroconium chaetospira* inoculated into the roots of the plants including seven species of Cruciferae, two species of Solanaceae, two species of Cucurbitaceae, Umbelliferae, Asteraceae, Malvaceae, and Chenopodiaceae, the fungus inhabited there as in the case of Chinese cabbages, cabbages, and 'chingensai'.

The present invention relates to a root endophyte capable of preventing soil-borne diseases, a process for producing the root endophytes, and a method for preventing soil-borne diseases of crops using the root endophytes. More specifically, it relates to:

(1) a root endophyte symbiotically living in roots of crops in the soil and capable of preventing soil-borne diseases of the crops;

(2) the root endophyte of (1), wherein said root endophyte is a microorganism belonging to the genus Heteroconium;

(3) the root endophyte of (2), wherein said microorganism belonging to the genus Heteroconium is *Heteroconium chaetospira*;

(4) the root endophyte of any one of (1) to (3), wherein said soil-borne disease is Verticillium diseases or club root diseases;

(5) a process for producing root endophytes capable of preventing soil-borne diseases, wherein the process comprises isolating, culturing, and classifying root endophytes symbiotically inhabiting in roots of crops cultivated on the soil, inoculating the isolates into the roots of the crops, inoculating the soil pathogenic fungi into the soil where the crops inoculated with the isolate are grown, growing the crops for the period required for development of the soil-borne disease, examining development of the disease, and identifying and selecting the inoculated isolates that showed a low incidence rate of soil-borne diseases;

(6) the process for producing root endophytes capable of preventing soil-borne diseases of (5), wherein the soil where the crops are cultivated for isolating symbiotes from their roots is culture soil free from agricultural chemicals;

(7) the process for producing root endophytes capable of preventing soil-borne diseases of (5) or (6), wherein *Heteroconium chaetospira* is isolated from cultured endophytes and classified based on morphology of its spores;

(8) a method for preventing soil-borne diseases of crops, wherein the method comprises inoculating root endophytes, which symbiotically live in roots of crops in the soil and are capable of preventing soil-borne diseases of crops, into the roots of the crop, allowing them to inhabit there, and growing the crops in the soil;

(9) a method for preventing soil-borne diseases of crops, wherein the method comprises sowing seeds of the crops on the cultured nursery where root endophytes symbiotically living in the roots of the crops are cultured, allowing the seeds to sprout to let the endophytes inhabit there, and cultivating the crops on the soil;

(10) the method for preventing soil-borne diseases of (8) or (9), wherein said soil-borne disease of crops is Verticillium diseases or club root diseases;

(11) the method for preventing soil-borne diseases of any one of (7) to (9), wherein said root endophyte to be inoculated in the roots of the crops is a microorganism belonging to the genus Heteroconium; and

(12) the method for preventing soil-borne diseases of (11), wherein said microorganism belonging to the genus Heteroconium are *Heteroconium chaetospira*.

The term "root endophytes" used herein means microorganisms inhabiting in roots of plants. In general, root endophytes are symbiotic with plants and never cause disease in the plants. The term "soil-borne diseases" means diseases that the subterranean part of the plant is infected with geophilic pathogenic fungi and bacteria. These pathogenic microorganisms sometimes invade the vessels of the plant and develop a systemic disease. The term "Verticillium disease" means a generic name of soil-borne diseases that show wilting of plants caused by fungi belonging to genus Verticillium. The term "club root disease" means a generic name of soil-borne diseases in which *Plasmodiophora brassicae* produces clubs (auxesis) in the subterranean part of the plant of Cruciferae.

In the present invention, although the root endophytes used for preventing soil-borne diseases include, without any limitations, any root endophyte as long as it is capable of preventing soil-borne diseases, microorganisms belonging to genus Heteroconium are preferable, with *Heteroconium chaetospira* being particularly preferable. The Verticillium disease and the club root disease are suitable examples of soil-borne diseases to which the endophytes of the present invention can be applied.

The crops to be treated by inoculating with the root endophytes of the present invention are not particularly limited. The root endophytes of the present invention are widely applicable to the crops including Cruciferae, Solanaceae, Cucurbitaceae, Umbelliferae, Asteraceae, Malvaceae and Chenopodiaceae. For example, the root endophytes of the present invention may control the soil-borne diseases by applying them to the plants which are infected with Verticillium, including flowers such as *Physalis alkekengi* var. franchetii, monkshood, chrysanthemum, cosmos, pot marigold, and Iceland poppy; and vegetables such as okra, strawberry, spinach, 'udo', clotsfoot, burdock, turnip, radish, Chinese cabbage, eggplant, tomato, cucumber, melon, soybean, and potato, and the plants of Cruciferae which are infected with club root disease, such as Chinese cabbage, cabagge, 'chingensai', broccoli, radish, cauliflower, mustard, stock, rape, and water cress.

The root endophytes capable of preventing soil-borne diseases can be produced as follows. First, the root endophytes are isolated from the root of the crops cultivated in the soil, cultured, and classified. On this occasion, it is preferable to use agricultural chemicals-free culture soil that is not disinfected with chemicals for growing crops because various root endophytes can be obtained due to rich microbiota in such soil. Classification of root endophytes depend on the species of the microorganisms. Unidentifiable isolates may be classified based on, for example, colony types. If an isolate is *Heteroconium chaetospira*, it can be classified based on, for example, morphology of spores. The isolate is then inoculated into the roots of the crops, and the geophilic pathogenic fungus is inoculated into the soil while cultivating the crops. After the crops are grown for the period required for development of the soil-borne disease, development of soil-borne diseases is examined, and the endophytes inoculated into the root of the crops that show a low incidence rate of the soil-borne disease are identified and selected. The endophytes thus specified and selected as the one capable of preventing the soil-borne disease can be obtained in a large amount by culturing them in the medium such as PDA. The root endophytes obtained can be stored in a dormant state.

When the root endophytes obtained are used for preventing the soil-borne diseases, the method typically used comprises sowing seeds of the crop on the nursery where the root endophytes symbiotically living in the roots of the crop are cultured, allowing the seeds to germinate to let the endophytes inhabit in the roots of the crops, and growing the crop in the soil. Alternatively, the root endophytes can be directly inoculated into the roots of the crop, allowed to inhabit there while growing the crop in the soil.

BEST MODE FOR IMPLEMENTING THE INVENTION

The present invention is described in more detail with reference to the following examples, but is not construed to be limited thereto.

EXAMPLE 1
Identification of Root Endophytes Used for the Biological Control Test Seeds of Chinese cabbage were sown in the soil in which wheat and soybean had been continuously cropped. The plants were grown for about two months and then collected from the soil. The root tips of the Chinese cabbages were cut off, washed, and allowed to stand on the isolation medium (½ conc. of cornmeal agar). The colonies developed on the medium were then transferred to a storage medium (½ conc. of cornmeal agar supplemented with 10 g/l of wheat germ extract and 2 g/l of yeast extract) to serve as an isolate of the root endophyte. The isolates were identified and classified into species. Unidentifiable isolates were classified based on colony types.

Figure 2:
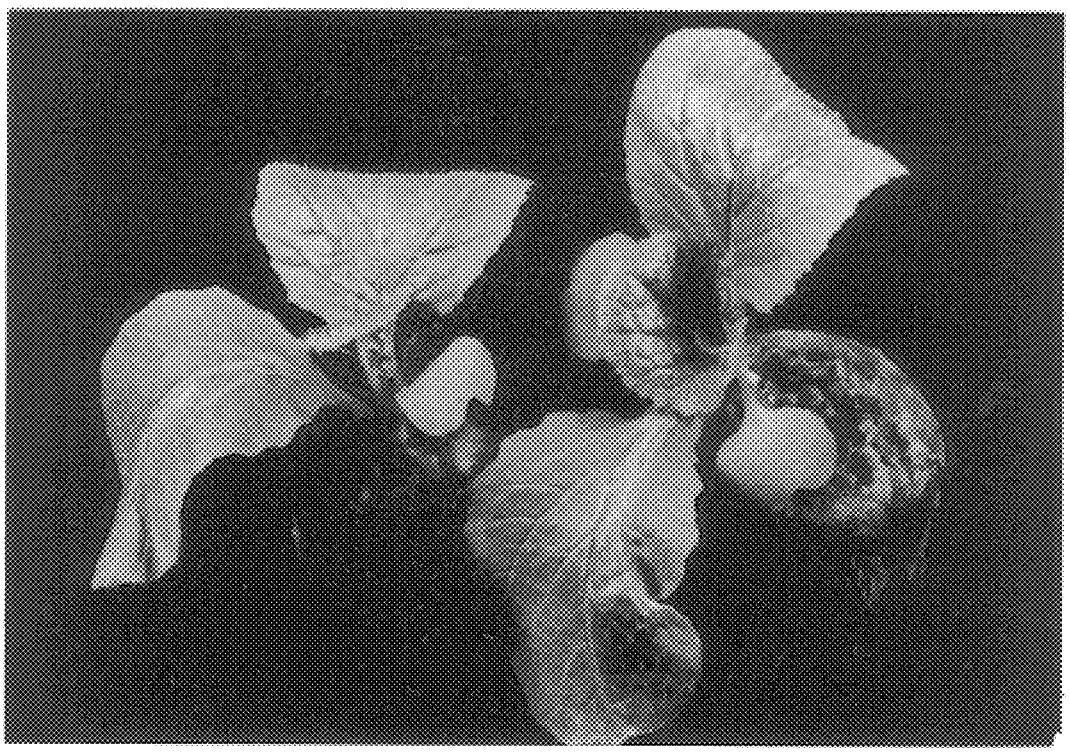
FIG. 2 is a photograph of seedling of Chinese cabbages in which the root endophytes have inhabited. Peat pellet in which the root endophytes were grown was used as culture soil.

The disease-preventing test was performed in the soil where Chinese cabbages were grown. Pellet formed by compressing and solidifying peatmoss (trade name: Jiffy-7, AS Jiffy products LTD., Norway) was soaked in the medium containing nutrients (10 g/l of wheat germ extract and 2 g/l of yeast extract) and was sterilized with steam. The test isolates were inoculated in the center of the pellet and cultured to prepare a nursery. Seeds of Chinese cabbage were sown on the nursery, and the seedlings were grown at room temperature for about three weeks to allow the endophytes inhabit in the roots (FIG. 2). The seedlings of the Chinese cabbages having the endophytes inhabited in their root were transferred in the field contaminated with pathogens causing the club root disease and the yellows in early September and were allowed to grow. The test was then conducted in middle of November.

As a result, several isolates showed a remarkable effect for preventing the yellows of the Chinese cabbage. Among them, the most effective isolate was identified based on morphology of spores as *Heteroconium chaetospira*. This fungus is a root endophyte that inhabits symbiotically in the roots of Chinese cabbages. This *Heteroconium chaetospira* strain (accession no. H4007) was deposited in the depository institute.

(1) Name and address of the depository institute:
   Name: National Institute of Bioscience and Human-Technology Agency of Industrial Science and Technology
   Address: 1–3, Higashi 1-chome, Tsukuba-shi, Ibaraki-ken 305, JAPAN
(2) Date of deposit (original deposit date): Mar. 13, 1997
(3) Accession number: FERM BP-6134

Figure 1A:
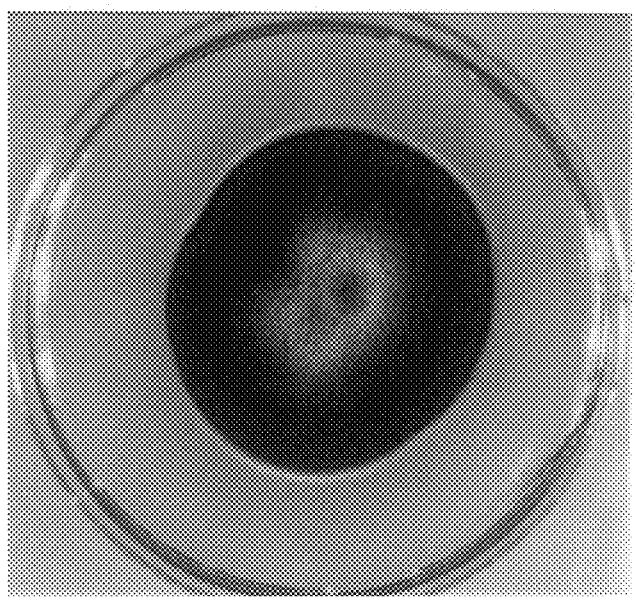
FIG. 1 shows the root endophyte (*Heteroconium chaetospira*) used in the present invention. In this figure, A is a photograph of colony on the medium, and B is a microscopic photograph of conidia formed on the colony.
Figure 1B:
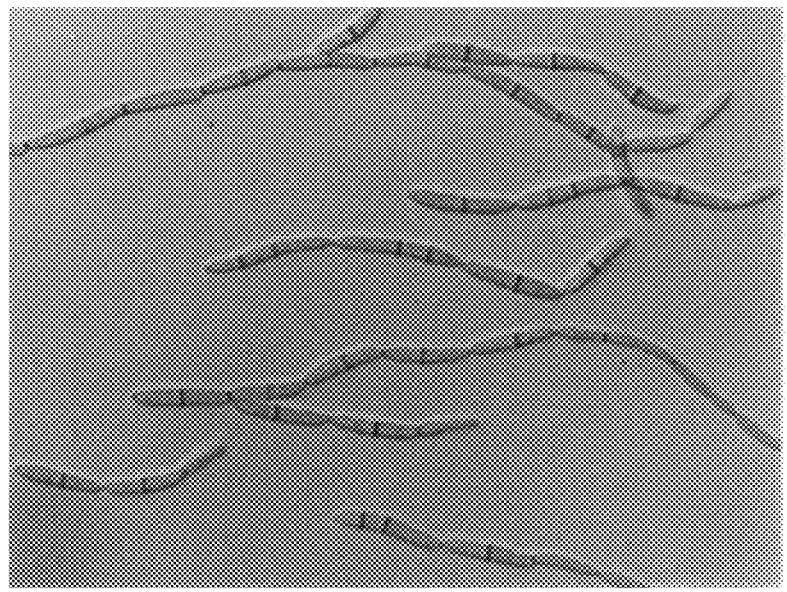

FIG. 1 shows a microscopic photograph of conidia of the root endophyte, which showed the efficacy for preventing the yellows of Chinese cabbages. Fifty of conidia and conidiophore were observed and their sizes and characteristics are as follows: The conidiophore extends perpendicularly from the aerohypha and has a septum, whose lower part is brown and its color becomes lighter towards the upper part. Its height ranges from 13.7 to 52.0 $\mu$m (mean, 28.8 $\mu$m) and its width ranges 2.3 to 4.9 $\mu$m (mean, 3.29 $\mu$m). A chain of conidia is formed at the tip of the conidiophore. The conidium is of the budding type and has cylindrical shape with both ends becoming narrow. The conidium consists of 0 to 4 cells and has no constriction in the septum. Its height ranges from 10.9 to 24.7 $\mu$m (mean, 16.9 $\mu$m) and its width ranges from 2.3 to 4.5 $\mu$m (mean, 3.3 $\mu$m). The conidia form a long chain and are easily separated from one another.

EXAMPLE 2
Preventing the Yellows of Chinese Cabbage Using *Heteroconium chaetospira*

The south-west part of Ibaraki Prefecture has been Chinese cabbage producing district for a long time and it frequently suffers from Verticillium diseases such as the yellows resulted from continuous cropping. Soil there has been disinfected using chemicals as measures for preventing the soil-born diseases. The amount of chemicals is increasing and thus a safe and labour-saving system of cultivation has been desired. In addition, to date, no variety resistant to the disease has been found. The efficacy of a root endophyte (*Heteroconium chaetospira*) was examined in the field by inoculating it into two varieties (strains) of Chinese cabbages with good qualities.

Pellet prepared by compressing and solidifying peatmoss (trade name: Jiffy-7, AS Jiffy products LTD., Norway) was soaked in the ME medium (10 g/l Malt extract, 2 g/l yeast extract) to allow it to absorb the medium (20 ml per pellet), then sterilized with steam at 121° C. for 30 minutes. The test endophyte was inoculated into the center of the pellet and incubated at 25° C. for a month in the dark to prepare a nursery. A control nursery was made by allowing pellet to absorb sterilized water. Seeds of Chinese cabbage were sown on the respective pellets and the plants were grown at 20 to 25° C. in the greenhouse. About three weeks later, the test endophyte was inoculated into the plants. FIG. 2 is a photograph of the seedlings of the Chinese cabbage in which the root endophyte inhabited in its roots.

The roots of the Chinese cabbage were collected about three months after the transfer of the seedlings and examined. The development of diseases was evaluated, employing the modified method of Yoshikawa et al. (Yoshikawa H, et al., 1977, Proceedings of Woronin+100 Conference, University of Wisconsin, Madison, 80–86) and using the following disease index. The disease development was classified into five levels from 0 to 4 and disease levels 1, 2, 3, and 4 were weighted by 10, 30, 60, and 100, respectively.

$$\text{Disease index} = \frac{\sum(\text{number of the plants for each index} \times \text{weight})}{\text{Total plant number}}$$

To obtain the efficacy of the root endophyte for preventing soil-borne diseases in the field, it is key to know how to make the test enndophyte inhabit in the plant. In the above test, the test isolate was inoculated into the pellet supplemented with medium and cultured at 25° C. for a month in the dark to prepare a nursery. Seeds of Chinese cabbage were sown on the nursery and grown in the greenhouse at 20 to 25° C. for about three weeks to allow the endophyte to inhabit efficiently in the roots of the seedlings. The seedlings of the Chinese cabbage were then transferred to the soil and cultivated.

Table 1 shows examples of Chinese cabbages, which had been inoculated with the root endophyte in their roots, cultivated in the severely infected field. Table 2 shows examples of cultivation in the moderately infected field. As shown in Table 1 and 2, *Heteroconium chaetospira* (*Heteroconium chaetospira*/strain number: H4007) effectively suppressed the development of the yellows not only in the moderately infected field but also in the severely infected field. To date, there has been no report of success in preventing diseases by this endophyte. On the other hand, comparative examples show cultivation of Chinese cabbages in the same field under the same conditions as above except for not using *Heteroconium chaetospira*. In the comparative examples, the yellows developed in high frequency. Since *Heteroconium chaetospira* was re-isolated from the roots of the Chinese cabbage, which had been inoculated with them, at such a high rate as 47% on the average, indicating that the endophyte inhabited in the plants even in the field. In addition, *Heteroconium chaetospira* was not isolated from aerial parts at all. This confirms safety of this method.

The incidence of the disease differs between the two varieties (strains) tested. The incidence in W4107 was lower than that of "Shnriso" (Table 1). Combination of W4107 and *Heteroconium chaetospira* showed the best effect for prevention of yellows of Chinese cabbages.

TABLE 1

| | | Disease index | |
|---|---|---|---|
| | variety of Chinese cabbage | External symptom | Internal symptom |
| Use of Heteroconium chaetospira | 'Shinriso' | 14.6 | 19.2 |
| Use of Heteroconium chaetospira | W4107 | 1 | 19 |
| Control | 'Shinriso' | 45 | 46.7 |
| Control | W4107 | 11.7 | 46.7 |

TABLE 2

| | | Disease index | |
|---|---|---|---|
| | variety of Chinese cabbage | External symptom | Internal symptom |
| Use of Heteroconium chaetospira | 'Shinriso' | 0 | 4.4 |
| Use of Heteroconium chaetospira | W4107 | 0 | 3 |
| Control | 'Shinriso' | 0 | 44 |
| Control | W4107 | 0 | 13.1 |

EXAMPLE 3

Investigation of the Mechanism of Preventing the Diseases

Figure 3A:
FIG. 3 is a microscopic photograph of the root endophytes that have inhabited in the roots (in the cortex cells) of Chinese cabbages. In this figure, A shows hyphae of the root endophyte in the root apex, while B shows the invasion process of the root endophyte into a cell of Chinese cabbage, in which an appressorium and a hypha are observed.
Figure 3B:

To investigate how *Heteroconium chaetospira* prevents soil-borne diseases of crops, the roots in which this endophyte had inhabited was stained with a 0.005% Cotton blue solution (50% acetic acid) and observed under a microscope. The results demonstrated that *Heteroconium chaetospira* invaded mainly from the root apex and settle down in the cortex cells as shown in FIG. 3. The arrow in the FIG. 3A indicates a hypha of the root endophyte (*Heteroconium chaetospira*).

That *Heteroconium chaetospira* settles down in the root apex is particularly important for preventing soil-borne diseases. There has been no report to date of a root endophyte like *Heteroconium chaetospira* that can invade into plant cells and settle down there to live symbiotically with its host.

This endophyte does not inhabit in all the parts of root. Nevertheless, infection with soil-borne pathogens is not detected even in the parts where this endophyte is not observed. This may be because inhabitation of this endophyte in the roots confers resistance on plants against other pathogens.

EXAMPLE 4

Effect of the Root Endophyte (*Heteroconium chaetospira*) on Club Root Diseases of Chinese Cabbages, Cabbages, and 'chingensai'

Pellet prepared by compressing and solidifying peatmoss (trade name: Jiffy-7, AS Jiffy products LTD., Norway) was soaked in the ME medium (10 g/l Malt extract, 2 g/l yeast extract), allowed to absorb the medium (20 ml per pellet), and sterilized with steam at 121° C. for 30 minutes. The test endophyte was inoculated into the center of the pellet and incubated at 25° C. for a month in the dark to prepare a nursery. A control nursery was made by allowing the pellet to absorb sterilized water. Seeds of Chinese cabbage, cabbage, and 'chingensai' were sown on the respective pellets and grown at 20 to 250 C. in the greenhouse. About three weeks later, the test endophyte was inoculated therein.

The roots of the Chinese cabbage, cabbage, and 'chingensai' were collected about 2 months after the transfer of the seedlings and they were examined. The development of the diseases was evaluated according to the modified method of Yoshikawa et al. (Yoshikawa H, et al., 1977, Proceedings of Woronin+100 Conference, University of Wisconsin, Madison, 80–86) using the following disease index. The disease development was classified into four levels from 0 to 3 and disease levels 1, 2, and 3 were weighted by 20, 60, and 100, respectively. Sixteen individual plants were used for the test.

As the result, this endophyte was effective for preventing the club root diseases of Chinese cabbage, cabbage, and 'chingensai' as indicated in Table 3, suggesting that it is also effective against the clob root disease of all the vegetables belonging to Cruciferae.

TABLE 3

| Treatment | Test plants | Disease index |
|---|---|---|
| H. chaetospira | Chinese cabbage | 23 |
| | cabbage | 10 |
| | 'chingensai' | 39 |
| Control | Chinese cabbage | 100 |
| | cabbage | 15 |
| | 'chingensai' | 90 |

EXAMPLE 5

Application of the Root Endophyte to Other Crops

As described in Examples 2 and 3, the root endophyte (*Heteroconium chaetospira*) prevented the yellows of Chinese cabbage, conferring resistance on the plant by inhabiting in the host plant and inhibiting subsequent invasion by pathogens. This suggested that the root endophyte (*Heteroconium chaetospira*) can prevent other diseases with the same mechanism if only it inhabits in the test plants. Endophytes have their own host range and are generally classified by the family of the host plants. *Heteroconium chaetospira* was tested if it can inhabit in plants other than Cruciferae. Specifically, *Heteroconium chaetospira* was tested as to whether it can inhabit in the roots of the plants of seven species from Cruciferae, two species from Solanaceae, two species from Cucurbitaceae, Umbelliferae, Asteraceae, Malvaceae, and Chenopodiaceae, which are indicated in Table 4, in addition to Chinese cabbage, cabbage and 'chingensai'.

Seeds of the plants listed in Table 4, which were sterilized on their surface, were sown in the peatmoss pellet in which *Heteroconium chaetospira* had been cultured. The plants were grown for about 1 month at 20° C., in 80% humidity, for 16 hours in the light and 8 hours in the dark and then transferred to the planters. They were grown subsequently for about 1 month in the planters. The test plants were then collected and their root tips were cut off at about 1 cm from the apex, washed, and allowed to stand on the isolation medium (½ conc. of cornmeal agar) in the petri dish (9 cm diameter). Thereafter, the colonies developed on the medium were transferred onto the subculture/storage medium (½ conc. of cornmeal agar supplemented with 10 g/l of malt extract and 2 g/l of yeast extract) and they were compared with the isolate for inoculation. The experiment was performed three times and 45 pieces of root tips were examined in total.

As a result, *Heteroconium chaetospira* was found to settle down in all the plants examined. In Table 4, the rate of settling down was calculated by dividing the number of root tips, from which colonies of root endophyte were developed on the medium, by the total number of the root tips tested.

TABLE 4

| Test plants | Rate of settling down (%) |
|---|---|
| Cruciferae | |
| broccoli | 89 |
| cabbage | 95 |
| radish | 56 |
| cauliflower | 89 |
| mustard | 56 |
| stock | 56 |
| rape | 22 |
| water cress | 44 |
| Solanaceae | |
| eggplant | 30 |
| tomato | 56 |
| Cucurbitaceae | |
| melon | 56 |
| watermelon | 56 |
| Umbelliferae | |
| carrot | 33 |
| Asteraceae | |
| lettuce | 89 |
| Malvaceae | |
| okra | 22 |
| Chenopodiaceae | |
| spinach | 93 |

As described above, the root endophyte can be used to prevent a wide range of soil-borne diseases including the yellows of Chinese cabbages and other soil-borne diseases of the flowers and vegetables.

Industrial Applicability

As described above, the present invention enables preventing soil-borne diseases using the root endophytes which inhabit symbiotically in the roots of plants and are capable of preventing soil-borne diseases such as Verticillium diseases and club root diseases. Since this method can prevent soil-borne diseases taking advantage of functions in the nature, the geophilic pathogens of crops can be controlled without chemicals. The methods for preventing soil-borne diseases with less harmful influence on humans and environment.

What is claimed is:

1. A method of decreasing the susceptibility of a plant to a soil-borne disease, the method comprising inoculating a root of a plant with a fungus belonging to the genus Heteroconium.

2. The method of claim 1, wherein the fungus is a strain of *Heteroconium chaetospira*.

3. The method of claim 2, wherein the fungus is deposited at the National Institute of Bioscience and Human-Technology Agency of Industrial Science and Technology, Japan, and has accession number FERM BP-6134.

* * * * *

UNITED STATES PATENT AND TRADEMARK OFFICE
CERTIFICATE OF CORRECTION

PATENT NO. : 6,306,390 B1
DATED : October 23, 2001
INVENTOR(S) : Kazuhiko Narisawa It is certified that error appears in the above-identified patent and that said Letters Patent is hereby corrected as shown below:

Column 4,
Line 49, delete "cabagge" and insert -- cabbage --

Column 7,
Line 18, delete "enndophyte" and insert -- endophyte --

Column 8,
Line 52, delete "250C" and insert -- 25ºC --

Column 9,
Line 1, delete "clob" and insert -- club --

Signed and Sealed this

Fifth Day of April, 2005

JON W. DUDAS
*Director of the United States Patent and Trademark Office*